(12) United States Patent
Weinberger

(10) Patent No.: US 6,605,030 B2
(45) Date of Patent: *Aug. 12, 2003

(54) APPARATUS AND METHOD FOR TREATING A DISEASE PROCESS IN A LUMINAL STRUCTURE

(75) Inventor: Judah Z. Weinberger, Teaneck, NJ (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/188,724

(22) Filed: Nov. 9, 1998

(65) Prior Publication Data

US 2002/0055709 A1 May 9, 2002

(51) Int. Cl.[7] ................................................ A61N 5/00
(52) U.S. Cl. .................. 600/3; 604/96.01; 604/101.01; 604/509
(58) Field of Search ............................ 604/265, 53, 96, 604/101, 104, 507, 509, 264, 103.02, 101.01, 101.02, 523; 606/194–196, 49; 600/1–8

(56) References Cited

U.S. PATENT DOCUMENTS

| 5,059,166 A | 10/1991 | Fischell et al. | |
|---|---|---|---|
| 5,199,939 A | 4/1993 | Dake et al. | |
| 5,213,561 A | 5/1993 | Weinstein et al. | |
| 5,302,168 A | 4/1994 | Hess | |
| 5,411,466 A | 5/1995 | Hess | |
| 5,616,114 A | * 4/1997 | Thornton et al. | 600/3 |
| 5,643,171 A | * 7/1997 | Bradshaw et al. | 600/1 |
| 5,653,683 A | * 8/1997 | D'Andrea | 604/21 |
| 5,674,177 A | 10/1997 | Hehrlein et al. | |
| 5,681,289 A | * 10/1997 | Wilcox et al. | 604/175 |
| 5,720,717 A | * 2/1998 | D'Andrea | 604/20 |
| 5,782,740 A | * 7/1998 | Schneiderman | 600/1 |
| 5,782,742 A | 7/1998 | Crocker et al. | |
| 5,833,650 A | * 11/1998 | Imaran | 604/53 |
| 5,840,008 A | 11/1998 | Klein | |
| 5,863,285 A | * 1/1999 | Coletti | 600/3 |
| 5,902,299 A | * 5/1999 | Jayaraman | 606/20 |
| 5,908,407 A | * 6/1999 | Frazee et al. | 604/101 |
| 5,910,101 A | * 6/1999 | Andrews et al. | 600/3 |
| 5,916,143 A | * 6/1999 | Apple et al. | 600/3 |
| 5,954,693 A | * 9/1999 | Barry | 604/96 |
| 5,976,106 A | * 11/1999 | Verin et al. | 604/96 |
| 5,985,307 A | * 11/1999 | Hanson et al. | |
| 6,135,981 A | * 10/2000 | Dyke | |

FOREIGN PATENT DOCUMENTS

| WO | 9622121 | 7/1996 |
|---|---|---|
| WO | WO-98/01185 | * 1/1998 |

* cited by examiner

Primary Examiner—Brian L. Casler
Assistant Examiner—Kevin C. Sirmons
(74) Attorney, Agent, or Firm—John P. White; Cooper & Dunham LLP

(57) ABSTRACT

An apparatus and method for treating a disease process in a luminal structure comprises a balloon catheter having a central balloon and two edge balloons. The central balloon may be separately inflated temporally and with different radioactive fluid than the edge balloons. Other arrangements include a wire, stent and concentric balloons, which provide spatial and temporal control enabling differential radioactivity at different spatial locations along the structure.

18 Claims, 3 Drawing Sheets

APPARATUS AND METHOD FOR TREATING A DISEASE PROCESS IN A LUMINAL STRUCTURE

The present invention relates to an apparatus and method for treating or preventing a disease process in a luminal structure such as a blood vessel.

Various devices have been proposed and used for angioplasty and restenosis in a luminal structure, such as a vein or artery of a patient. Typically, angioplasty is performed using a balloon catheter. After angioplasty, restenosis can develop in the luminal structure. Balloon injury of the luminal structure, caused by balloon inflation, treated with sublethal doses of radiation stimulates cell proliferation and decreases restenosis. Preliminary information from human trials has indicated that restenosis is inhibited by doses of radioactive isotopes, e.g., of 15–45 Gy, to the wall of the luminal structure. Radioisotopes have been used to treat restenosis, such as by inflating the balloon with a fluid containing a radioisotope.

Human studies suggest that a problem with decreased radiation dose occurs at the edge of the balloon treatment zone, where a combination of subtherapeutic radiation doses combine with balloon or stent trauma to stimulate neointimal proliferation.

SUMMARY OF THE INVENTION

It is an object of the present invention to provide an apparatus and method for providing temporal control of radioactive doses in treating or preventing restenosis.

It is an object of the present invention to provide spatial control of radioactive doses in treating or preventing restenosis.

It is an object of the present invention to provide differential temporal and spatial control of radioactive doses in treating or preventing restenosis.

It is an object of the present invention to minimize arterial trauma from vascular angioplasty devices such as balloons in the region of subtherapeutic dose delivered.

It is an object of the present invention to provide an apparatus and method for mitigating injury in the luminal structure of a patient in areas of diminished radiation dose.

It is an object of the present invention to provide an apparatus capable of spatially varying the deliverable dose of radiation, including, for example, providing an increased dose or boost of radiation on the edges relative to the middle.

It is an object of the present invention to provide a catheter having a multi-segmented radiation dose delivery structure, such as a balloon.

As used herein, the term "treating" or "treatment" includes treating or treatment of a disease process as well as preventing or inhibiting a disease process. As used herein, the term "vicinity" in connection with a luminal structure, includes in the luminal structure and near the luminal structure.

According to one aspect of the invention, an apparatus for treating a disease process in the vicinity of a luminal structure is provided, comprising a catheter shaft, and a radioactive material carrier providing a spatially varying radioactivity along the length of the shaft.

In accordance with another aspect of the present invention, an apparatus for treating a disease process in the vicinity of a luminal structure is provided, comprising a catheter shaft having at least first and second inflation lumens defined longitudinally therein, a first balloon mounted on said shaft and in fluid communication with the first inflation lumen, and a second balloon mounted on said shaft at a different longitudinal position from said first balloon and in fluid communication with the second inflation lumen, to thereby allow separate inflation and deflation of said first and second balloon segments.

According to another aspect of the invention, an apparatus is provided for treating a disease process in the vicinity a luminal structure, comprising a catheter shaft having at least first and second inflation lumens defined longitudinally therein a central balloon mounted on said shaft and in fluid communication with the first inflation lumen and two edge balloons mounted on said shaft on either side of the central balloon, both edge balloons being in fluid communication with the second inflation lumen.

According to another aspect of the invention, a method for treating a disease process in the vicinity of a luminal structure is provided, comprising positioning inside a luminal structure a source of radioactive material having spatially varying distribution, and removing the source of radioactive material after a treatment period.

According to another aspect of the invention, a method for treating a disease process in the vicinity of a luminal structure is provided, comprising providing a balloon catheter having at least two separably inflatable balloons mounted on a catheter shaft at different longitudinally positions on the shaft, inserting the balloon catheter into the luminal structure of a subject, inflating the two balloons separately with radioactive fluid, removing the respective radioactive fluid from the two balloons and removing the balloon catheter from the luminal structure.

According to another aspect of the invention, a method for treating a disease process in the vicinity of a luminal structure is provided, comprising providing a balloon catheter having at least three inflatable balloons mounted on a catheter shaft at different longitudinally positions on the shaft, including a middle balloon and two side balloons at opposite sides of the middle balloon, inserting the balloon catheter into the luminal structure of a subject, inflating the balloons with radioactive fluid by inflating the middle balloon separately from the two side balloons, removing the radioactive fluid from the middle balloon and two side balloons and removing the balloon catheter from the luminal structure.

Other objects and advantages will become more apparent when considering the following detailed description of a preferred embodiment, accompanying claims and drawing.

DETAILED DESCRIPTION OF THE PREFERRED EMBODIMENT

Figure 1:
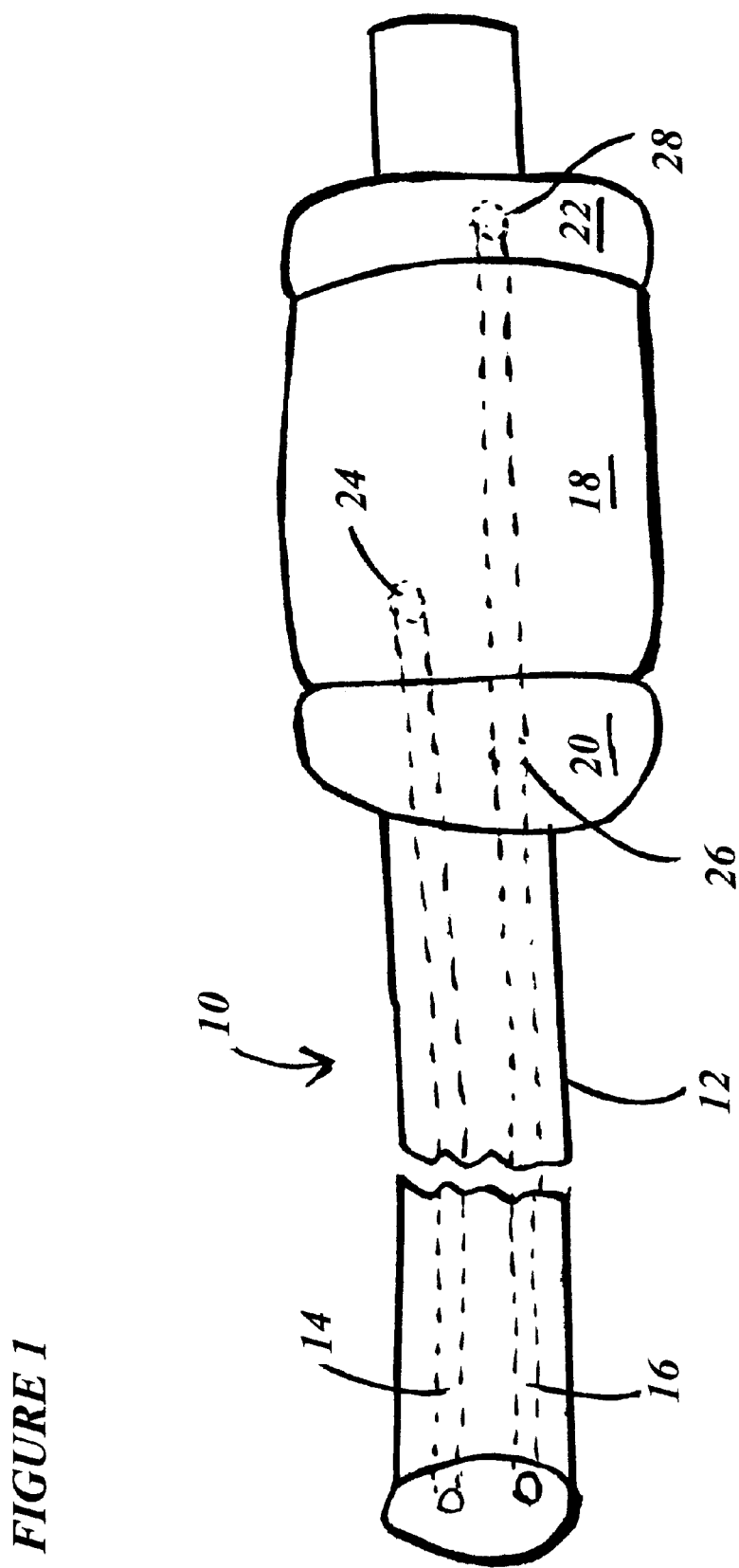
FIG. 1 shows a variable dosage device in the form of a balloon catheter according to one embodiment of the invention.

According to one aspect of the invention, an apparatus for treating a disease process in the vicinity of a luminal structure is provided comprising a catheter shaft, and a radioactive material carrier providing a spatially varying radioactivity along the length of the shaft.

The radioactive material carrier may comprise a balloon having a circumferential dimension which varies longitudinally along the length of the shaft, and having a radioactive fluid contained therein.

The balloon may have a middle region and two edge regions, said middle region having a larger diameter than the two edge regions.

The radioactive material carrier may comprise a wire.

The radioactive material may be in the form of pellets on the wire.

The radioactive material may be in the form of a coating on the wire.

The radioactive material carrier may be a stent.

The stent may have a middle region and edge regions, wherein the radioactivity in the middle region is higher than the edge regions.

The stent may have a middle region and edge regions, wherein the radioactivity in the edge regions is higher than the middle region.

The radioactive material carrier may comprise two balloons wherein one balloon is arranged inside the other balloon.

Relatively higher radioactivity fluid may be in the outer balloon and relatively lower radioactivity fluid may be in the inner balloon.

According to another aspect of the invention, an apparatus is provided for treating a disease process in the vicinity of a luminal structure, comprising a catheter shaft having at least first and second inflation lumens defined longitudinally therein a first balloon mounted on said shaft and in fluid communication with the first inflation lumen and a second balloon mounted on said shaft at a different longitudinally position from said first balloon, and in fluid communication with the second inflation lumen, to thereby allow separate inflation and deflation of said first and second balloon segments.

The first balloon may have a diameter larger than the second balloon.

A third balloon may be mounted on said shaft at a different longitudinal position than said first and second balloons, to thereby provide three balloon segments arranged longitudinally spaced, with one balloon in the middle and two side balloons on respective sides of said one balloon.

The respective side balloons may be in communication with a common inflation lumen, and wherein the middle balloon is in fluid communication with a different inflation lumen.

The middle balloon may be longer than the side balloons.

According to another aspect of the invention, an apparatus is provided for treating a disease process in the vicinity of a luminal structure, comprising a catheter shaft having at least first and second inflation lumens defined longitudinally therein a central balloon mounted on said shaft and in fluid communication with the first inflation lumen and two edge balloons mounted on said shaft on either side of the central balloon, both edge balloons being in fluid communication with the second inflation lumen.

According to another aspect of the invention, a method for treating a disease process in the vicinity of a luminal structure is provided, comprising positioning inside a luminal structure a source of radioactive material having a spatially varying distribution, and removing the source of radioactive material after a treatment period.

The step of positioning a source of radioactive material may comprise providing a source of radioactive material in a carrier having a central region and edge regions, said central region having a larger circumferential dimension than said edge regions, said central region contacting the luminal structure, and said edge region not contacting the luminal structure.

The carrier may be a balloon having a larger diameter in the central region than in the edge regions.

The step of positioning may comprise providing a source of radioactive material in a carrier in the form of a wire having radioactive material along its length.

The step of positioning may comprise providing a source of radioactive material in the form of a stent having radioactive material along its length.

The step of positioning may comprise an inner balloon and an outer balloon larger than and enclosing the inner balloon, wherein radioactive fluid is provided in the outer balloon.

According to another aspect of the invention, a method for treating a disease process in the vicinity of a luminal structure is provided, comprising providing a balloon catheter having at least two separably inflatable balloons mounted on a catheter shaft at different longitudinally positions on the shaft, inserting the balloon catheter into the luminal structure of a subject, inflating the two balloons separately with radioactive fluid, removing the respective radioactive fluid from the two balloons and removing the balloon catheter from the luminal structure.

The step of inflating the two balloons separately may be done at two different times.

The step of inflating the two balloons separately may be done with radioactive fluid having different radioactivity.

According to another aspect of the invention, a method for treating a disease process in the vicinity of a luminal structure is provided, comprising providing a balloon catheter having at least three inflatable balloons mounted on a catheter shaft at different longitudinally positions on the shaft, including a middle balloon and two side balloons at opposite sides of the middle balloon, inserting the balloon catheter into the luminal structure of a subject, inflating the balloons with radioactive fluid by inflating the middle balloon separately from the two side balloons, removing the radioactive fluid from the middle balloon and two side balloons and removing the balloon catheter from the luminal structure.

The step of inflating the middle balloon and two side balloons may be done at two different times.

The step of inflating the middle balloon may be done with radioactive fluid having different radioactivity than the fluid for the two side balloons.

The radioactive fluid for the two side balloons may have a higher activity of radioisotope than the radioactive fluid for the middle balloon.

The step of inflating may include inflating the two side balloons together.

The step of inflation may include inflating the two side balloons separately.

Referring now to FIG. 1, a balloon catheter 10 is shown having a shaft 12 having at least two inflation lumens 14 and 16. Also mounted on the shaft is a central or middle inflation balloon 18 and two edge inflation balloons 20 and 22. The central or middle inflation balloon 18 is in communication with inflation port 24 which is communication with inflation lumen 14.

The edge inflation balloons 20 and 22 are in communication with inflation ports 26, 28, respectively, which are both in communication with inflation lumen 16. The central balloon 18 can thus be inflated and deflated separately from the two edge inflation balloons 20 and 22. The central balloon 18 can be differentially inflated temporally and/or with varying activity radioisotope fluid solutions than edge inflation balloons 20 and 24. Thus, one can "boost" the edge dose from the radioisotope in the edge balloons 20 and 24, relative to the dose in the central balloon 18, and allow fall off of dose in non-dilated segments of the artery.

Of course, the two edge balloons may be inflated separably from each other if separate inflation lumens to them are provided. Additional balloons or sections of a balloon may also be provided, either individually inflatable through their own respective inflation lumens, or in various combinations using common inflation lumens. For example, a first set of spatially alternating balloon segments may be connected together, and the remaining, alternating balloon segments may also be connected together. The balloon segments may have different longitudinal lengths, or be sized or shaped in different ways allowing flexibility of use depending on the application.

Figure 2:
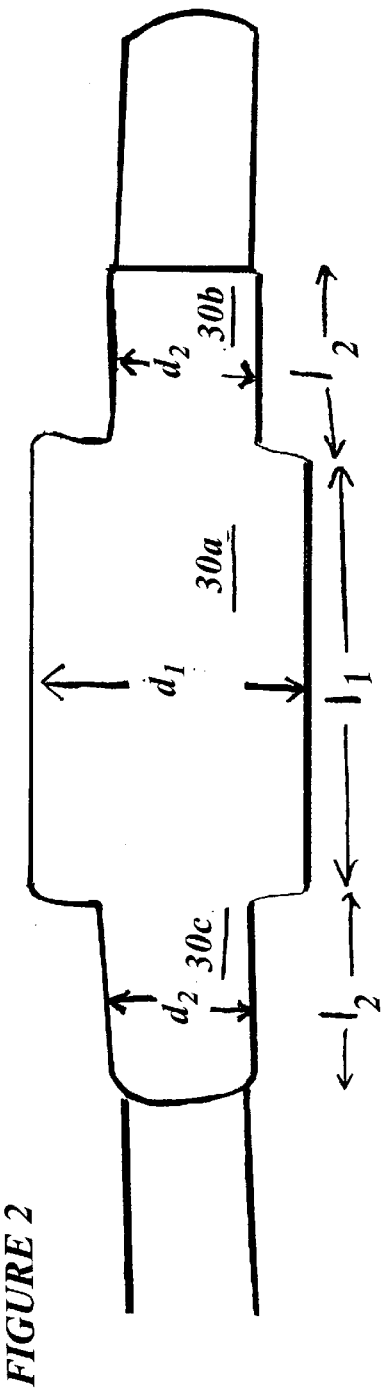
FIG. 2 shows a variable dosage device in the form of a balloon catheter according to another embodiment of the invention.

FIG. 2 shows another embodiment according to the invention for providing variable dose delivery. Here a balloon has at least two segments of different sizes. A first segment 30a has a diameter $d_1$ and length $l_1$ and a second segment 30b having a diameter $d_2$ and length $l_2$, where $d_1$ is different from, in this case greater than, $d_2$. A third segment 30c is provided which has diameter $d_3$ and length $l_3$. In the embodiment illustrated $d_2$ is substantially the same as $d_3$ and $l_2$ is substantially the same as $l_3$. This arrangement provides a primary treatment region corresponding to the location of the first segment 30a, and at least one secondary treatment region corresponding to one or both segments 30b and 30c.

The entire balloon 30 may be inflated by a single inflation lumen and inflation port which inflates the entire balloon, wherein the balloon is formed to inflate to different diameters in different sections under the same internal fluid pressure, by providing different compliant material, for the different sections, or the same material but wherein the sections 30b and 30c is prestretched. Other ways to provide different sized balloon sections will occur to those skilled in the art. Segment 30a is arranged to contact the inner wall of the luminal structure when inflated, whereas segments 30b and 30c do not contact the inner wall of the luminal structure when inflated, thereby avoiding any trauma that may be caused if such balloon sections 30b and 30c were to contact the inner wall of the luminal structure.

Figure 3:
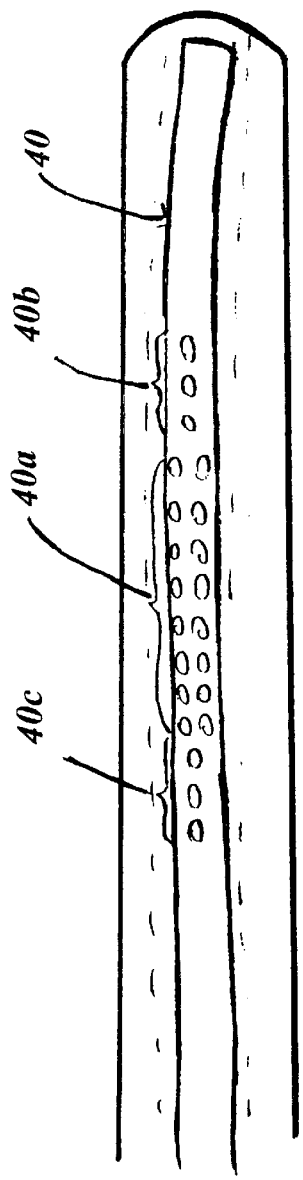
FIG. 3 shows a variable dosage device in the form of a wire having different dosages along its length.

FIG. 3 shows another embodiment according to the invention for providing variable dose delivery. Here the catheter receives a wire having different radioactive dosages along its length. In the embodiment illustrated, the wire has pellets mounted in different densities in different regions. In the center region 40a, the density is greater then the density of edge regions 40b and 40c. Another way to achieve the same result would be to provide pellets of different radioactive material in the different regions and keeping the density of the pellets the same. Instead of pellets, the radioactive material can be in the form of a coating on the wire, absorbed into or activated on or in the wire, or combination of pellets, coating or other way of providing radioactive material on and/or integral with the wire, and the activity of the radioisotope may be different in the different regions. The different radioactivity may vary axially, longitudinally or in some other spatial manner.

Figure 4:
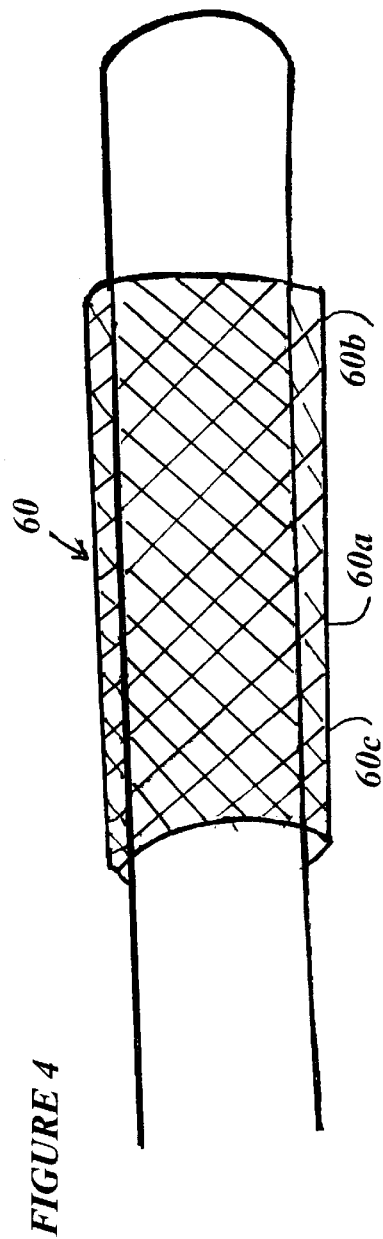
FIG. 4 shows a radioactive stent having differential sputter density zones, with a relatively high dosage activity zone in the middle and two relatively lower dosage activity zones of the edges.

FIG. 4 shows another embodiment according to the invention in the form of a radioactive stent 60 having a central portion 60a having a higher radioactivity dose than the two side edges 60b and 60c. The central portion may have a lower radioactivity dose than the two side edges. Other differential dose arrangements may be provided. The radioactivity differential may be provided by varying the amount, thickness or otherwise vary the quantity of material, which may for example be in the form of a coating, on the stent. The differential may be achieved by providing different radioisotopes.

Figure 5:
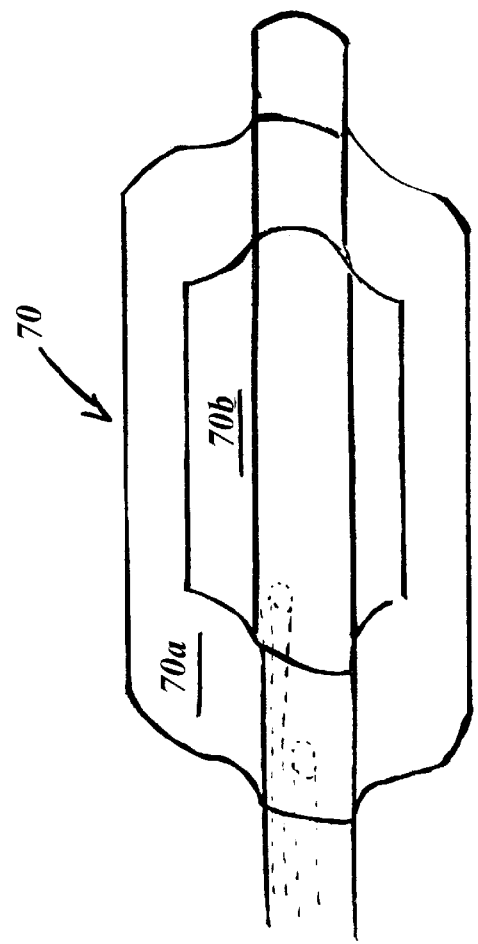
FIG. 5 shows a radioactive balloon arrangement in the form of two differentially sized and shaped concentric balloons.

FIG. 5 shows another embodiment of the invention comprising a balloon structure 70 having an outer balloon 70a and an inner balloon 70b. The inner balloon 70b and outer balloon 70a are substantially concentric. The volume between the inner and outer balloons, which may be called an outer region, is inflated with radioactive fluid, and the inner volume of the inner balloon, which may be called an inner region, may be inflated with non-radioactive fluid, or radioactive fluid with a lower activity than the radioactive fluid for the outer region, to thereby provide a higher radioactivity at the edges relative to the middle. The outer edges of the outer balloon may gently taper to meet the catheter shaft.

It must be noted that although the present invention is described by reference to particular embodiments thereof, many changes and modifications of the invention may become apparent to those skilled in the art without departing from the spirit and scope of the invention as set forth in the claims.

I claim:

1. An apparatus for treating a disease process in the vicinity of a luminal structure, comprising:
   a catheter shaft having at least first and second inflation lumens defined longitudinally therein;
   a first balloon mounted on said shaft and in fluid communication with the first inflation lumen;
   a second balloon mounted on said shaft immediately adjacent to contacting and abutting and at a different and non-overlapping longitudinal position from and non-nested with said first balloon, and in fluid communication with the second inflation lumen, to thereby allow separate inflation and deflation of said first and second balloon segments; and
   a radioactive fluid for at least one of the balloons, wherein said balloon contains the radioactive fluid.

2. The apparatus according to claim 1, wherein the first balloon has a diameter different from the second balloon.

3. The apparatus according to claim 1, further including a third balloon mounted on said shaft at a different longitudinal position than said first and second balloons, to thereby provide three balloon segments arranged longitudinally spaced, with one balloon in the middle and two side balloons on respective sides of said one balloon.

4. The apparatus according to claim 2, wherein the respective side balloons are in communication with a common inflation lumen, and wherein the middle balloon is in fluid communication with a different inflation lumen.

5. The apparatus according to claim 2, wherein the middle balloon is longer than the side balloons.

6. An apparatus for treating a disease process in the vicinity of a luminal structure, comprising:

a catheter shaft having at least first and second inflation lumens defined longitudinally therein;

a central balloon mounted on said shaft and in fluid communication with the first inflation lumen;

two edge balloons non-nested with each other and said central balloon and mounted on said shaft on either side of and non-overlapping with and immediately adjacent to, contacting and abutting the central balloon, both edge balloons being in fluid communication with the second inflation lumen separate from said first inflation lumen; and a radioactive fluid for at least one of the balloons, wherein said balloon contains the radioactive fluid.

7. A method for treating a disease process in the vicinity of a luminal structure, comprising:

providing a balloon catheter having at least two separately inflatable balloons mounted immediately adjacent to each other on a catheter shaft at different longitudinal positions on the shaft each of said balloons being in fluid communication with a separate inflation lumen and the balloons not being in fluid communication with each other;

inserting the balloon catheter into the luminal structure of a subject;

providing a radioactive fluid;

inflating the two balloons separately through two separate inflation lumens with the radioactive fluid, wherein the balloons contain the radioactive fluid;

removing the respective radioactive fluid from the two balloons; and removing the balloon catheter from the luminal structure.

8. The method according to claim 7, wherein the step of inflating the two balloons separately is done at two different times.

9. The method according to claim 7, wherein the step of inflating the two balloons separately is done with radioactive fluid having different radioactivity.

10. A method for treating a disease process in the vicinity of a luminal structure, comprising:

providing a balloon catheter having at least three inflatable balloons mounted immediately adjacent each other on a catheter shaft at different longitudinally positions on the shaft, including a middle balloon and two side balloons at opposite sides of the middle balloon;

inserting the balloon catheter into the luminal structure of a subject;

providing a radioactive fluid;

inflating the balloons with the radioactive fluid by inflating the middle balloon separately from the two side balloons;

removing the radioactive fluid from the middle balloon and two side balloons; and removing the balloon catheter from the luminal structure.

11. The method according to claim 10, wherein the step of inflating the middle balloon and two side balloons is done at two different times.

12. The method according to claim 10, wherein the step of inflating comprises inflating the middle balloon with radioactive fluid having different radioactivity than the fluid for the two side balloons.

13. The method according to claim 12, wherein the radioactive fluid for the two side balloons has a higher activity of radioisotope than the radioactive fluid for the middle balloon.

14. The method according to claim 10, wherein the step of inflating comprises inflating the two side balloons together.

15. The method according to claim 10, wherein the step of inflating comprises inflating the two side balloons separately.

16. An apparatus for treating a disease process in the vicinity of a luminal structure, comprising:

a catheter shaft having at least first and second inflation lumens defined longitudinally therein;

a central balloon mounted on and fully encircling said shaft and in fluid communication with the first inflation lumen; and two edge balloons mounted on and fully encircling said shaft on either side of and immediately adjacent to the central balloon, both edge balloons being in fluid communication with the second inflation lumen.

17. A method for treating a disease process in the vicinity of a luminal structure, comprising:

providing a balloon catheter having at least two separably inflatable balloons mounted immediately adjacent each other on a catheter shaft at different longitudinal positions on the shaft;

inserting the balloon catheter into the luminal structure of a subject;

providing a radioactive fluid;

inflating the two balloons separately with radioactive fluid, wherein the balloons contain the radioactive fluid;

removing the respective radioactive fluid from the two balloons; and removing the balloon catheter from the luminal structure.

18. A method for treating a disease process in the vicinity of a luminal structure, comprising:

providing a balloon catheter having at least three inflatable balloons mounted on a catheter shaft at different longitudinally positions on the shaft, including a middle balloon and two side balloons at opposite sides of and immediately adjacent to the middle balloon;

inserting the balloon catheter into the luminal structure of a subject;

providing a radioactive fluid;

inflating the balloons with the radioactive fluid by inflating the middle balloon separately from the two side balloons, wherein the balloons contain the radioactive fluid;

removing the radioactive fluid from the middle balloon and two side balloons; and removing the balloon catheter from the luminal structure.

* * * * *